US008023734B2

(12) United States Patent
Jolly et al.

(10) Patent No.: US 8,023,734 B2
(45) Date of Patent: Sep. 20, 2011

(54) 3D GENERAL LESION SEGMENTATION IN CT

(75) Inventors: Marie-Pierre Jolly, Hillsborough, NJ (US); Leo Grady, Yardley, PA (US)

(73) Assignee: Siemens Aktiengesellschaft, München ( * ) Notice: Subject to any disclaimer, the term of this patent is extended or adjusted under 35 U.S.C. 154(b) by 690 days.

(21) Appl. No.: 12/128,676

(22) Filed: May 29, 2008

(65) Prior Publication Data

US 2009/0097727 A1 Apr. 16, 2009

Related U.S. Application Data

(60) Provisional application No. 60/978,818, filed on Oct. 10, 2007.

(51) Int. Cl.
*G06K 9/34* (2006.01)
(52) U.S. Cl. ........ 382/171; 382/103; 382/128; 382/131; 382/154; 382/173
(58) Field of Classification Search .................. None
See application file for complete search history.

(56) References Cited

U.S. PATENT DOCUMENTS

| | | | | |
|---|---|---|---|---|
| 5,903,664 | A * | 5/1999 | Hartley et al. | 382/154 |
| 6,690,816 | B2 * | 2/2004 | Aylward et al. | 382/128 |
| 6,754,376 | B1 * | 6/2004 | Turek et al. | 382/131 |
| 6,973,212 | B2 * | 12/2005 | Boykov et al. | 382/173 |
| 7,574,031 | B2 * | 8/2009 | Dehmeshki | 382/131 |
| 7,583,831 | B2 * | 9/2009 | Tu et al. | 382/131 |
| 7,596,267 | B2 * | 9/2009 | Accomazzi et al. | 382/173 |
| 7,620,226 | B2 * | 11/2009 | Unal et al. | 382/128 |
| 7,643,663 | B2 * | 1/2010 | Wiemker et al. | 382/131 |
| 7,702,153 | B2 * | 4/2010 | Hong et al. | 382/173 |
| 7,720,268 | B2 * | 5/2010 | Slabaugh et al. | 382/128 |
| 7,724,954 | B2 * | 5/2010 | Fluck et al. | 382/173 |
| 7,773,807 | B2 * | 8/2010 | Grady et al. | 382/173 |
| 2002/0172407 | A1 * | 11/2002 | O'Donnell et al. | 382/131 |
| 2003/0035507 | A1 * | 2/2003 | Hsu et al. | 378/4 |
| 2005/0163375 | A1 | 7/2005 | Gardy | |
| 2006/0153435 | A1 * | 7/2006 | Wallmark et al. | 382/129 |
| 2006/0211940 | A1 * | 9/2006 | Antonelli et al. | 600/410 |
| 2006/0228009 | A1 * | 10/2006 | Fidrich et al. | 382/128 |
| 2006/0262960 | A1 * | 11/2006 | Le Clerc et al. | 382/103 |
| 2007/0058865 | A1 * | 3/2007 | Li et al. | 382/173 |
| 2007/0248250 | A1 * | 10/2007 | Gulsun et al. | 382/128 |
| 2008/0100621 | A1 * | 5/2008 | Aharon et al. | 345/424 |
| 2008/0144943 | A1 * | 6/2008 | Gokturk et al. | 382/224 |
| 2008/0187198 | A1 * | 8/2008 | Grady et al. | 382/128 |
| 2008/0260221 | A1 * | 10/2008 | Unal et al. | 382/128 |
| 2008/0260229 | A1 * | 10/2008 | Mashiach | 382/131 |

(Continued)

OTHER PUBLICATIONS

Xu, Qing; Chen, Hong; Zhang, Li and Novak, C. L., "Automatic corpus callosum segmentation for standardized MR brain scanning," Medical Imaging 2007: Image Processing, p. 65123K, Feb. 2007.*

(Continued)

*Primary Examiner* — Vu Le
*Assistant Examiner* — Xuemei Chen
(74) *Attorney, Agent, or Firm* — Donald B. Paschburg

(57) ABSTRACT

A general purpose method to segment any kind of lesions in 3D images is provided. Based on a click or a stroke inside the lesion from the user, a distribution of intensity level properties is learned. The random walker segmentation method combines multiple 2D segmentation results to produce the final 3D segmentation of the lesion.

6 Claims, 9 Drawing Sheets

U.S. PATENT DOCUMENTS

| | | | |
|---|---|---|---|
| 2008/0292164 A1* | 11/2008 | Azar et al. | 382/131 |
| 2008/0298682 A1* | 12/2008 | Cocosco et al. | 382/173 |
| 2008/0310716 A1* | 12/2008 | Jolly et al. | 382/173 |
| 2008/0317308 A1* | 12/2008 | Wu et al. | 382/128 |
| 2008/0317314 A1* | 12/2008 | Schwartz et al. | 382/131 |
| 2009/0003672 A1* | 1/2009 | Maier et al. | 382/128 |
| 2009/0052756 A1* | 2/2009 | Saddi et al. | 382/131 |
| 2009/0080728 A1* | 3/2009 | Socher et al. | 382/131 |
| 2009/0136103 A1* | 5/2009 | Sonka et al. | 382/128 |
| 2009/0148012 A1* | 6/2009 | Altmann et al. | 382/128 |
| 2009/0175527 A1* | 7/2009 | Agliozzo et al. | 382/132 |
| 2009/0226037 A1* | 9/2009 | Yang et al. | 382/103 |
| 2010/0266170 A1* | 10/2010 | Khamene et al. | 382/128 |
| 2010/0278405 A1* | 11/2010 | Kakadiaris et al. | 382/131 |

OTHER PUBLICATIONS

"WHO Handbook for Reporting Results of Cancer Treatment", *World Health Organization*, (1979), 46 pp.

Therasse, Patrick et al., "New Guidelines to Evaluate the Response to Treatment of Solid Tumors", *Journal of the National Cancer Institute*, vol. 92, No. 3, (Feb. 2, 2000), pp. 205-216.

Yim, Peter J., et al., "Volumetry of Hepatic Metastases in Computed Tomography Using the Watershed and Active Contour Algorithms", *16th IEEE Symposium on Computer-Based Medical Systems*, (2003), 7 pp.

Bilello, Michel et al., "Automatic Detection and Classification of Hypodense Hepatic Lesions on Contrast-Enhanced Venous-Phase CT", *Med. Phys. 31* (9), (Sep. 2004), pp. 2584-2593.

Dornheim, Jana et al., "Segmentation of Neck Lymph Nodes in CT Datasets with Stable 3D Mass-Spring Models", *Proc. MICCAI*, (2006), pp. 904-911.

Unal, G. et al., "Semi-Automatic Lymph Node Segmentation in LN-MRI", *IEEE*, (2006), pp. 77-80.

Udupa, Jayaram K., et al., "Fuzzy Connectedness and Object Definition: Theory, Algorithms, and Applications in Image Segmentation", *Graphical Models and Image Processing*, vol. 58, No. 3, (May 1996), pp. 246-261.

Herman, Gabor T., et al., "Multiseeded Segmentation Using Fuzzy Connectedness", *IEEE Transactions on Pattern Analysis and Machine Intelligence*, Vo. 23, No. 5, (May 2001), pp. 460-474.

Grady, Leo "Random Walks for Image Segmentation", *IEEE Transactions on Pattern Analysis and Machine Intelligence*, vol. 28, No. 11, (Nov. 2006), pp. 1-17.

Grady, Leo et al., "An Energy Minimization Approach to the Data Driven Editing of Presegmented Images/Volumes", *Proceedings of Medical Image Computing and Computer-Assisted Intervention—MICCAI*, (2006), pp. 888-895.

Li, Yuanzhong et al., "A Machine Learning Approach for Locating Boundaries of Liver Tumors in CT Images", *IEEE*, (2006), 4 pp.

\* cited by examiner

3D GENERAL LESION SEGMENTATION IN CT

CROSS-REFERENCE TO RELATED APPLICATIONS

This application claims the benefit of U.S. Provisional Application No. 60/978,818, filed Oct. 10, 2007, which is incorporated herein by reference.

BACKGROUND OF THE INVENTION

The present invention relates to methods and apparatus for image segmentation for separation of a foreground object from a background. In particular, it relates to interactive 3D segmentation of an object from a background.

Cancer is the second leading cause of death in the United States as half a million people die each year. For this reason, it is important to diagnose the disease as early as possible and monitor it carefully as it is being treated. In addition to primary tumors, physicians are also interested in secondary tumors that might have metastasized through the rest of the body. The main areas of concern are the liver (because many forms of cancer generate liver metastases) and lymph nodes (because cancers spread through the lymphatic system).

The current standards to measure lesions for cancer monitoring are the WHO and RECIST criteria. The first criterion was proposed in 1979 by the World Health Organization in its "WHO handbook for reporting results of cancer treatment," and measures a tumor in two dimensions by its maximum diameter in an axial image multiplied by its largest perpendicular diameter in the same image.

In 2000, the Response Evaluation Criteria in Solid Tumor (RECIST) in P. Therasse, S. G. Arbuck, E. A. Eisenhauer, J. Wanders, R. S. Kaplan, L. Rubinstein, J. Verweij, M. van Glabbeke, A. T. van Oosterom, M. C. Christian, and S. G. Gwyther, "New guidelines to evaluate the response to treatment in solid tumors," Journal of the National Cancer Institute, vol. 92, no. 3, pp. 205-216, 2000, stated that the maximum diameter in an axial image alone could be used to quantify tumor sizes. It has been shown, however, that volume measurements provide more accurate estimates of the lesion sizes than one- and two-dimensional criteria as described in L. van Hoe, E. van Cutsem, I. Vergote, A. L. Baert, E. Bellon, P. Dupont, and G. Marchal, "Size quantification of liver metastases in patients undergoing cancer treatment: reproducibility of one-, two-, and three-dimensional measurements determined with spiral CT," Radiology, vol. 202, no. 3, pp. 671-675, 1997.

A lesion may be characterized in size and/or shape by different characteristics. These characteristics may include: volume, RECIST diameter, orthogonal diameter, WHO criterion, maximum 3D diameter, Z-extent, eccentricity, mean Hounsfield Unit, standard deviation of the Hounsfield Unit. These characteristics may be determined from a 3D segmentation of a lesion in 3D image data. Other characteristics may also be used.

Unfortunately, there are no good tools available to measure lesion volumes and it is very time consuming to manually outline them in 3D. Accordingly, novel and improved methods and systems for segmentation which from a single click inside or a stroke through the lesion can produce a 3D segmentation are required.

SUMMARY OF THE INVENTION

One aspect of the present invention presents a novel method and system that will provide a segmentation of an object from a background in 3D image data.

In accordance with another aspect of the present invention, a method is provided for segmentation of an object from a background in three-dimensional (3D) image data, comprising initiating a plurality of seeds in the object in a two-dimensional (2D) representation of the 3D image, of which at least one seed defines the object; determining a distribution of intensity levels of pixels in the 2D representation of the 3D image relative to an intensity level of a seed, segmenting the object from the background in a 2D representation of the 3D image based on the distribution of intensity levels into a first 2D segmentation contour; establishing a 2D segmentation contour of the object in at least two additional 2D representations of the image, each 2D representation containing a seed in the object, and creating a 3D segmentation contour of the object by applying a random walker segmentation method to all pixels in the 3D image, using pixels inside the 2D segmentation contours as object pixels and pixels outside the 2D segmentation contours as background pixels.

In accordance with a further aspect of the present invention, a method is provided for segmentation of an object from a background in three-dimensional (3D) image data, further comprising determining a cost image $C_L$ associated with the at least one seed in the 2D representation of the object; and determining an object histogram $H_L$ associated with the cost image as the distribution of intensity levels of pixels.

In accordance with another aspect of the present invention, a method is provided for segmentation of an object from a background in three-dimensional (3D) image data, further comprising computing a response image of the 2D representation of the object.

In accordance with a further aspect of the present invention, a method is provided for segmentation of an object from a background in a 2D representation of the three-dimensional (3D) image data, wherein the response image can be computed by applying an expression $$g(x, y) = \begin{cases} H_L(f(x, y))\left(1 - \dfrac{C_L(x, y)}{C_L^{max}}\right) & \text{if } L(x, y) = 1 \\ H_L(f(x, y))/2 & \text{if } L(x, y) = 0. \end{cases}$$

In accordance with another aspect of the present invention, a method is provided for segmentation of an object from a background in three-dimensional (3D) image data, further comprising, determining a background histogram $H_B$ for pixels not being part of the object in the 2D representation.

In accordance with a further aspect of the present invention, a method is provided for segmentation of an object from a background in three-dimensional (3D) image data, wherein the establishing of a 2D segmentation contour of the object in at least two additional 2D representations of the 3D image data using a response image that can be computed from an expression $g(x, y) =$ $$\begin{cases} g(x, y) & \text{if } H_L(f(x, y)) > H_B(f(x, y)) \\ \text{else} \\ \dfrac{3H_L(f(x, y))}{4}\left(1 - \dfrac{C_L(x, y)}{C_L^{max}}\right) & \text{if } L(x, y) = 1 \\ H_L(f(x, y))/4 & \text{if } L(x, y) = 0. \end{cases}$$

In accordance with another aspect of the present invention, a method is provided for segmentation of an object from a background in three-dimensional (3D) image data, wherein the 3D image data is provided by a CT scanner.

In accordance with a further aspect of the present invention, a method is provided for segmenting an object from a background in three-dimensional (3D) image data, comprising placing a plurality of seeds defining the object in a first two-dimensional (2D) representation of the 3D image data, determining a first 2D segmentation contour based on the plurality of seeds, determining a second 2D segmentation contour in a second 2D representation of the 3D image data and a third 2D segmentation contour in a third 2D representation of the 3D image data, determining a 3D segmentation contour of the object by applying a segmentation process to the 3D image data, using pixels inside the first, the second and the third 2D segmentation contours as 3D object seeds and pixels outside the first, the second and the third 2D segmentation contours as 3D background seeds.

In accordance with another aspect of the present invention, a method is provided for segmenting an object from a background in three-dimensional (3D) image data, wherein the segmentation process is a random walker segmentation process.

In accordance with a further aspect of the present invention, a method is provided for segmenting an object from a background in three-dimensional (3D) image data, wherein the plurality of seeds include a stroke of seeds and further includes a fourth 2D segmentation contour that is determined in a 2D representation comprising the stroke and is perpendicular to the first 2D representation.

In accordance with another aspect of the present invention, a method is provided for segmenting an object from a background in three-dimensional (3D) image data, wherein determining the first 2D segmentation contour includes a step of computing a cost of a best path between a plurality of seeds and every pixel in the 2D representation of the 3D image data.

In accordance with a further aspect of the present invention, a method is provided for segmenting an object from a background in three-dimensional (3D) image data, wherein determining the first 2D segmentation contour includes a step of computing a response image.

In accordance with another aspect of the present invention, a method is provided for segmenting an object from a background in three-dimensional (3D) image data, further comprising updating a distribution of intensities of pixels in object and background after determining a segmentation contour in a 2D representation of the 3D image data.

In accordance with another aspect of the present invention, a system is provided for segmentation of an object from a background in three-dimensional (3D) image data, comprising, a processor, a memory readable by the processor, the memory comprising program code executable by the processor, the program code adapted to perform the following steps: placing a plurality of seeds defining the object in a first two-dimensional (2D) representation of the 3D image data, determining a first 2D segmentation contour based on the plurality of seeds, determining a second 2D segmentation contour in a second 2D representation of the 3D image data and a third 2D segmentation contour in a third 2D representation of the 3D image data, determining a 3D segmentation contour of the object by applying a segmentation process to the 3D image data, using pixels inside the first, the second and the third 2D segmentation contours as 3D object seeds and pixels outside the first, the second and the third 2D segmentation contours as 3D background seeds.

In accordance with a further aspect of the present invention, a system is provided for segmentation of an object from a background in three-dimensional (3D) image data, wherein the segmentation process is a random walker segmentation process.

In accordance with another aspect of the present invention, a system is provided for segmentation of an object from a background in three-dimensional (3D) image data, wherein the plurality of seeds include a stroke of seeds and further including a fourth 2D segmentation contour that is determined in a 2D representation comprising the stroke and that is perpendicular to the first 2D representation.

In accordance with a further aspect of the present invention, a system is provided for segmentation of an object from a background in three-dimensional (3D) image data, wherein determining the first 2D segmentation contour includes a step of computing a cost of a best path between a plurality of seeds and every pixel in the 2D representation of the 3D image data.

In accordance with another aspect of the present invention, a system is provided for segmentation of an object from a background in three-dimensional (3D) image data, wherein determining the first 2D segmentation contour includes a step of computing a response image.

In accordance with a further aspect of the present invention, a system is provided for segmentation of an object from a background in three-dimensional (3D) image data, further comprising: calculating from the 3D segmentation contour of the object at least one characteristic of the object of the group of characteristics consisting of: volume, RECIST diameter, orthogonal diameter, WHO criterion, 3D maximum diameter, Z-extent, eccentricity, mean Hounsfield Unit, and standard deviation of the Hounsfield Unit.

DESCRIPTION OF A PREFERRED EMBODIMENT

Figure 1:
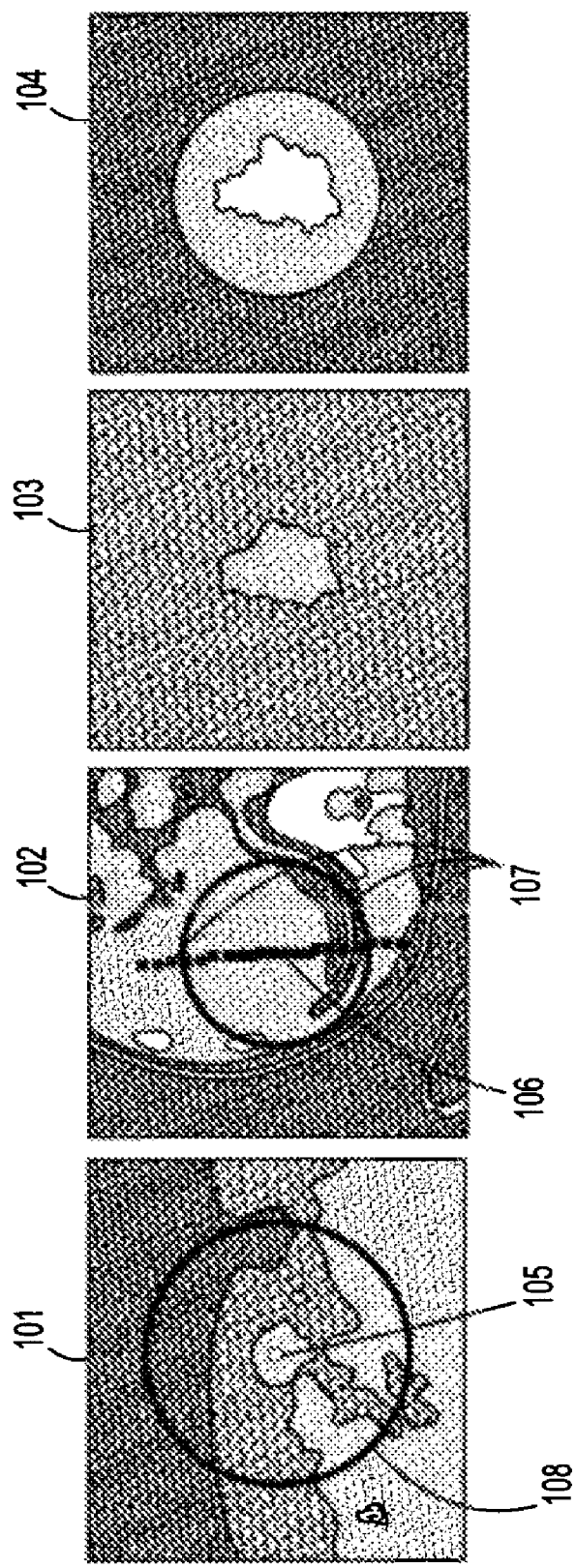
FIG. 1 illustrates a series of steps performed in accordance with one aspect of the present invention.

Most of the work on medical analysis for cancer screening and treatment has been in the context of lung cancer, mammography, and colon cancer. There has been very little interest in liver lesion segmentation though some research is described in P. J. Yim and D. J. Foran, "Volumetry of hepatic metastases in computed tomography using the watershed and active contour algorithms," in Proc. IEEE Symposium on Computer-Based Medical Systems, New York, N.Y., 2003, pp. 329-335, and in M. Bilello, S. B. Gokturk, T. Desser, S. Napel, R. B. Jeffrey Jr., and C. F. Beaulieu, "Automatic detection and classification of hypodense hepatic lesions on contrast-enhanced venous-phase CT," Medical Physics, vol. 31, no. 9, pp. 2584-2593, 2004. Earlier work has focused on relatively simple hypodense liver tumors or metastases which are nicely contrasted against the parenchyma. Papers have presented very simple image processing techniques (thresholding, watershed, active contours) which have been tested on very few examples. Of note is the work in Y. Li, S. Hara, and K. Shimura, "A machine learning approach for locating boundaries of liver tumors in {CT} images", Proc. Int. Conf. on Pattern Recognition, vol. 1, pp. 400-403, 2006 which uses AdaBoost to learn 1-D profiles on 30 examples and segment 30 lesions in 2D. Unfortunately, no validation is presented.

Lymph node segmentation has received more attention in recent years (see for instance J. Dornheim, H. Seim, B. Preim, I. Hertel, and G. Strauss, "Segmentation of neck lymph nodes in CT datasets with stable 3D mass-spring models," in Proc. MICCAI, 2006, pp. 904-911, and G. Unal, G. Slabaugh, A. Ess, A. Yezzi, T. Fang, J. Tyan, M. Requardt, R. Krieg, R. Seethamraju, M. Harisinghani, and R. Weissleder, "Semi-automatic lymph node segmentation in LN-MRI," in Proc. Int. Conf. Image Processing, Atlanta, Ga., 2006, pp. 77-80, and references herein) with more mature techniques that have been tested on larger number of examples. The main disadvantage with techniques published so far is that they focus on one type of lesions and are not general. In clinical cases however, radiologists might want to look at primary tumors, some liver metastases, and the lymphatic system. Therefore, it is very useful to provide a single tool capable of segmenting any type of lesion.

This segmentation task presents various difficulties. First, sizes and shapes vary significantly among lesions. In addition, the lesion itself can be highly heterogeneous and contain calcifications or necrotic regions. Finally, lesions and in particular lymph nodes are adjacent to iso-intensity soft tissues and high contrast structures such as blood vessels. Herein, the focus primarily will be on liver lesions (tumors and metastases) and lymph nodes. The techniques described herein, as an aspect of the present invention, have also been applied and are applicable to a large number of other lesions.

Segmentation Method

The segmentation method is divided into three steps. First, the system learns a rough gray level distribution for the lesion based on the information provided by the clicked point or the stroke. Second, the lesion is segmented on the 2D plane on which the user interacted, as well as on other 2D planes orthogonal to it. After each 2D segmentation, the gray level distribution for the lesion and the background are updated. Third, the random walker algorithm followed by size preserving smoothing is used to produce the 3D segmentation. Pixels in a 2D plane of the 3D image data may be called a 2D representation of the 3D image data.

The random walker segmentation algorithm and process is provided by L. Grady in detail in U.S. patent application Ser. No. 11/029,442 filed on Jan. 5, 2005 which is incorporated herein by reference in its entirety.

Gray Level Distribution Estimation

Since lesions can be of any size or shape, it was decided to rely solely on an intensity model for the lesion. However, lesions are all different, so it is crucial to learn an accurate intensity model on the fly for the lesion currently being segmented. The fuzzy connectedness algorithm as described in J. K. Udupa and S. Samarasekera, "Fuzzy connectedness and object definition: Theory, algorithms, and applications in image segmentation," Graphical Models and Image Processing, vol. 58, no. 3, pp. 246-261, 1996, computes the cost of the best path between a set of seeds and every pixel in the image. In a sense it provides a measure of how strongly a pixel belongs to the regions defined by the seeds. An example is shown in FIG. 1 with images 101, 102, 103 and 104. The region seeds are defined by the user interaction (the click point 105 or the pixels on the stroke 106) while the background seeds are placed along a circle and in the prolongations 107 of the stroke. In accordance with a further aspect of the present invention the background seeds may be placed interactively by a user. The background seeds may also be placed automatically for instance by a computer program. The background seeds may for instance be placed in a circle based on a size of a stroke of foreground seeds. Other ways to automatically place background seeds, for instance using an assumption of a maximum size of a lesion, are also fully contemplated.

Multiseeded fuzzy connectedness is shown in FIG. 1. FIG. 1 image 101 shows click point seeds (105 for region, circle 108 for background); FIG. 1 image 102 shows stroke seeds (106 for region, 107 including circle for background); FIG. 1 image 103 shows lesion cost $C_L(x, y)$; and FIG. 1 image 104 shows Labels L(x, y).

Two modifications are applied to the traditional multi-region fuzzy connectedness segmentation as aspects of the present invention. First, the multi-seeded technique proposed by Herman and Carvalho as described in G. T. Herman and B. M. Carvalho, "Multiseeded segmentation using fuzzy connectedness," IEEE Trans. Pattern Analysis and Machine Intelligence, vol. 23, no. 5, pp. 460-474, 2001, is used where the regions compete as the paths are being built. Also, a different cost function is used. In the traditional fuzzy connectedness approach, one might use the mean and variance of the region gray levels to prevent a slow varying path to pass through regions with different statistics. In the problem of lesion segmentation however, it is very difficult to estimate these statistics ahead of time and it is incorrect to assume that the region gray levels are Gaussian. So, instead, the range of gray level intensities along the path as a cost function is used.

The algorithm using Dijkstra's approach is implemented with a heap to keep track of the current best path. At every pixel (x, y), the minimum intensity $F^m(x, y)$, the maximum intensity $F^M(x, y)$ and the cost C(x, y) along the current best path to that pixel are maintained. The information at its neighbor (i, j) is updated by:

$$F^m(i,j)=\min \{F^m(x,y), f(i,j)\},$$

$$F^M(i,j)=\max \{F^M(x,y), f(i,j)\},$$

$$C(i,j)=F^M(i,j)-F^m(i,j)$$

wherein f(i, j) is the gray level at pixel (i, j). This cost function favors paths that do not vary too much in gray level and therefore stay within one homogeneous region. Heterogeneous regions can still be recovered when each seed point on the stroke builds its own homogeneous region which, when all put together form a larger heterogeneous region.

The multiseeded algorithm as described in G. T. Herman and B. M. Carvalho, "Multiseeded segmentation using fuzzy connectedness," IEEE Trans. Pattern Analysis and Machine Intelligence, vol. 23, no. 5, pp. 460-474, 2001, outputs the cost image $C_L(x, y)$ which is the cost of reaching pixel (x, y) from a lesion seed, as well as a label image L(x, y)=1 if pixel (x, y) belongs to the lesion and is 0 otherwise. This is illustrated in for instance FIG. 1 image 103 which is the cost image and image 104 which is the label image. The lesion histogram $H_L$ is built by adding the gray value of every lesion labeled pixel a number of times inversely proportional to the cost at that pixel (i.e.: $100/C_L(x, y)$).

Figure 2:
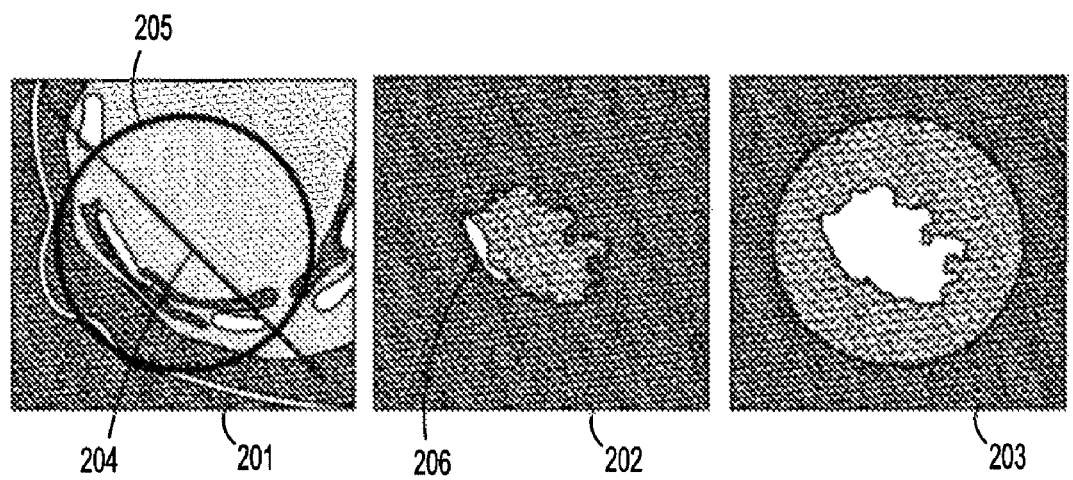
FIG. 2 provides another illustration of segmentation steps in accordance with an aspect of the present invention.

This method is not infallible and it could happen that an unknown region (belonging neither to the lesion nor to the background) gets labeled as lesion. This is illustrated in the image including a rib in FIG. 2. FIG. 2 has images 201, 202 and 203. Image 201 shows the highlighted seeding areas with stroke 204 for object and circle 205 for background seeds. Image 202 shows the segmentation including an unwanted area 206 with mislabeled pixels. Image 203 shows the segmentation area. To eliminate the wrong elements that might have been introduced in the lesion histogram, all modes in the histogram that are not sufficiently represented in the stroke are deleted.

2D Segmentation

Now that the lesion statistics are known, the response from the histogram $H_L(f(x, y))$ is evaluated at every pixel and combined with the cost function $C_L(x, y)$ from the fuzzy connectedness to compute the response image $g(x, y)$ in the following manner:

$$g(x, y) = \begin{cases} H_L(f(x, y))\left(1 - \dfrac{C_L(x, y)}{C_L^{max}}\right) & \text{if } L(x, y) = 1 \\ H_L(f(x, y))/2 & \text{if } L(x, y) = 0 \end{cases}$$

to emphasize the difference between the pixels inside the lesion, which respond well to the lesion histogram and have low cost, and the pixels outside the lesion.

Figure 3:
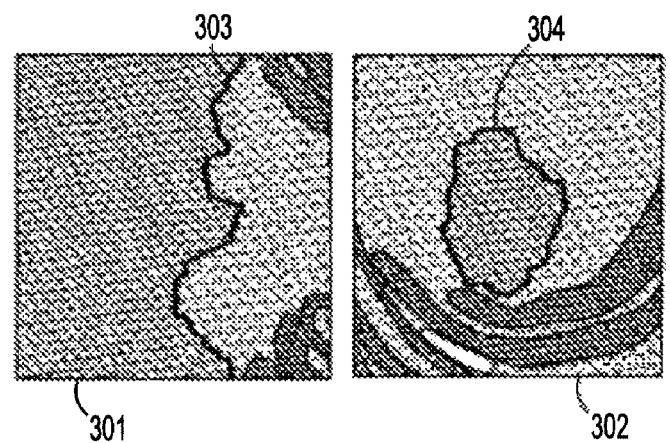
FIG. 3 provides an illustration of a segmentation step in accordance with an aspect of the present invention.

The image is converted to log-polar coordinates, its gradient is computed (using a 3×21 horizontal mask), and the 2D segmentation is recovered by finding the shortest path in the inverse of the gradient image. FIG. 3 shows the segmentation in the log-polar space in 301 with highlighted contour 303 and the corresponding contour 304 converted to the Cartesian space image 302.

Once the lesion has been segmented in the interaction plane, pixels inside the lesion are used to update the lesion histogram $H_L$ and pixels within 10 pixels outside the lesion are used to generate the background histogram $H_B$.

Figure 4:
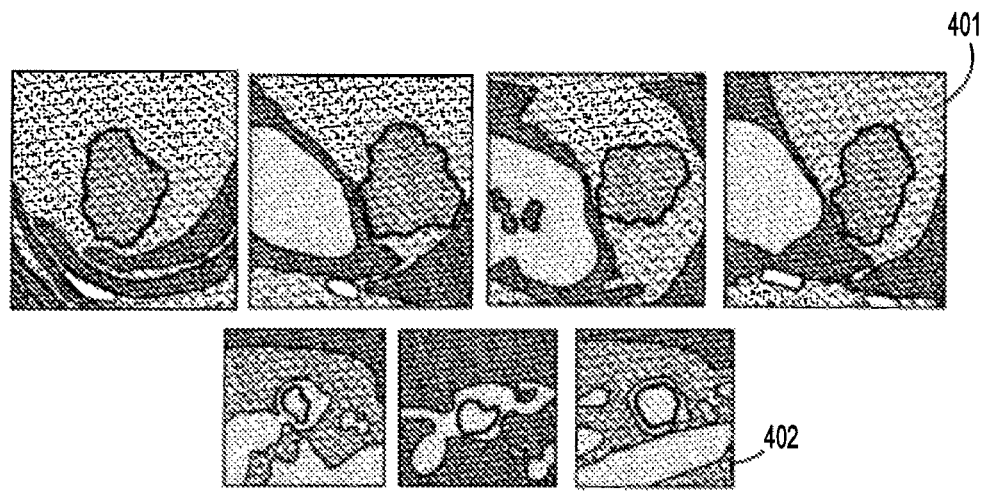
FIG. 4 provides an illustration of different 2D segmentations of an object in 3D image data in accordance with a further aspect of the present invention.

The segmented 2D contour is recovered in the same manner on the other planes. In the case of a clicked point, the two other main MPRs (multi-planar reconstructions) are processed. In the case of a stroke, the plane that is perpendicular to the stroke plane and also contains the stroke is also processed. FIG. 4 shows the results of the 2D segmentations (4 segmentations in image series 401 in 4 planes for a stroke and 3 segmentations in image series 402 in 3 planes for a click point). Since background statistics have now also been collected, the response image is now defined as:

$$g(x, y) = \begin{cases} g(x, y) & \text{if } H_L(f(x, y)) > H_B(f(x, y)) \\ \text{else} & \\ \dfrac{3H_L(f(x, y))}{4}\left(1 - \dfrac{C_L(x, y)}{C_L^{max}}\right) & \text{if } L(x, y) = 1 \\ H_L(f(x, y))/4 & \text{if } L(x, y) = 0 \end{cases}$$

3D Segmentation

Figure 5:
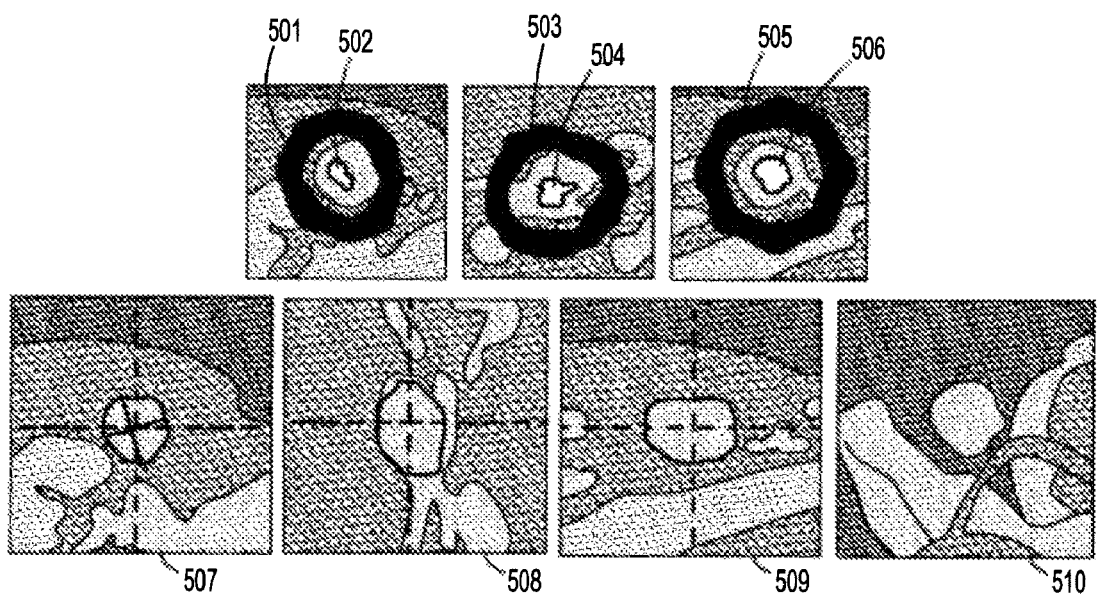
FIG. 5 illustrates creating a 3D segmentation of an object based on different 2D segmentation contours of the object in accordance with another aspect of the present invention.

The final step of the algorithm consists of applying the random walker segmentation algorithm provided by Grady in L. Grady, "Random walks for image segmentation," IEEE Trans. Pattern Analysis and Machine Intelligence, vol. 28, no. 11, pp. 1768-1783, 2006 and in the earlier cited U.S. patent application Ser. No. 11/029,442. The seeds for the random walker are generated directly from the 2D segmentations by simply choosing all the pixels that are a certain distance away from the segmentation boundaries as is shown in FIG. 5. In the three top images of FIG. 5 areas 502, 504 and 506 are the seeds for foreground or region to be segmented from the background. Areas 501, 503, and 505 are the seeds for the background. The algorithm computes the probability that a random walker initiating its walk at each voxel first arrives at a foreground seed before arriving at a background seed. It was shown in the above cited article by Grady that these probabilities can be efficiently computed by solving a sparse system of linear equations.

Typically, the random walker probabilities would be thresholded at 0.5 to produce the final binary segmentation. In accordance with an aspect of the present invention the following size preserving smoothing algorithm is provided. First, the size of the lesion is determined if the probabilities were to be thresholded at 0.5. Then, the probabilities are smoothed using a standard linearly separable Gaussian filter. Finally, the smoothed probabilities are thresholded at the level that leads to the same lesion size. The final segmentation result is shown in images 507, 508, 509 and 510 in the bottom part of FIG. 5.

Experiments and Results

115 CT datasets were collected from patients with various types of cancer. The datasets were acquired at 10 different clinical sites with different protocols and slice thicknesses ranging from 1 to 5 mm. Radiologists at the different hospitals identified and manually segmented a total of 293 lesions in these datasets. Among these lesions, there were 159 liver lesions, 98 lymph nodes, and 36 other lesions in lungs, pancreas, colon, ovaries, rectum, etc. The lesions ranged in size from 0.1 to 700 mL. Radiologists were asked to segment the lesions using the semi-automatic algorithm.

Figure 6:
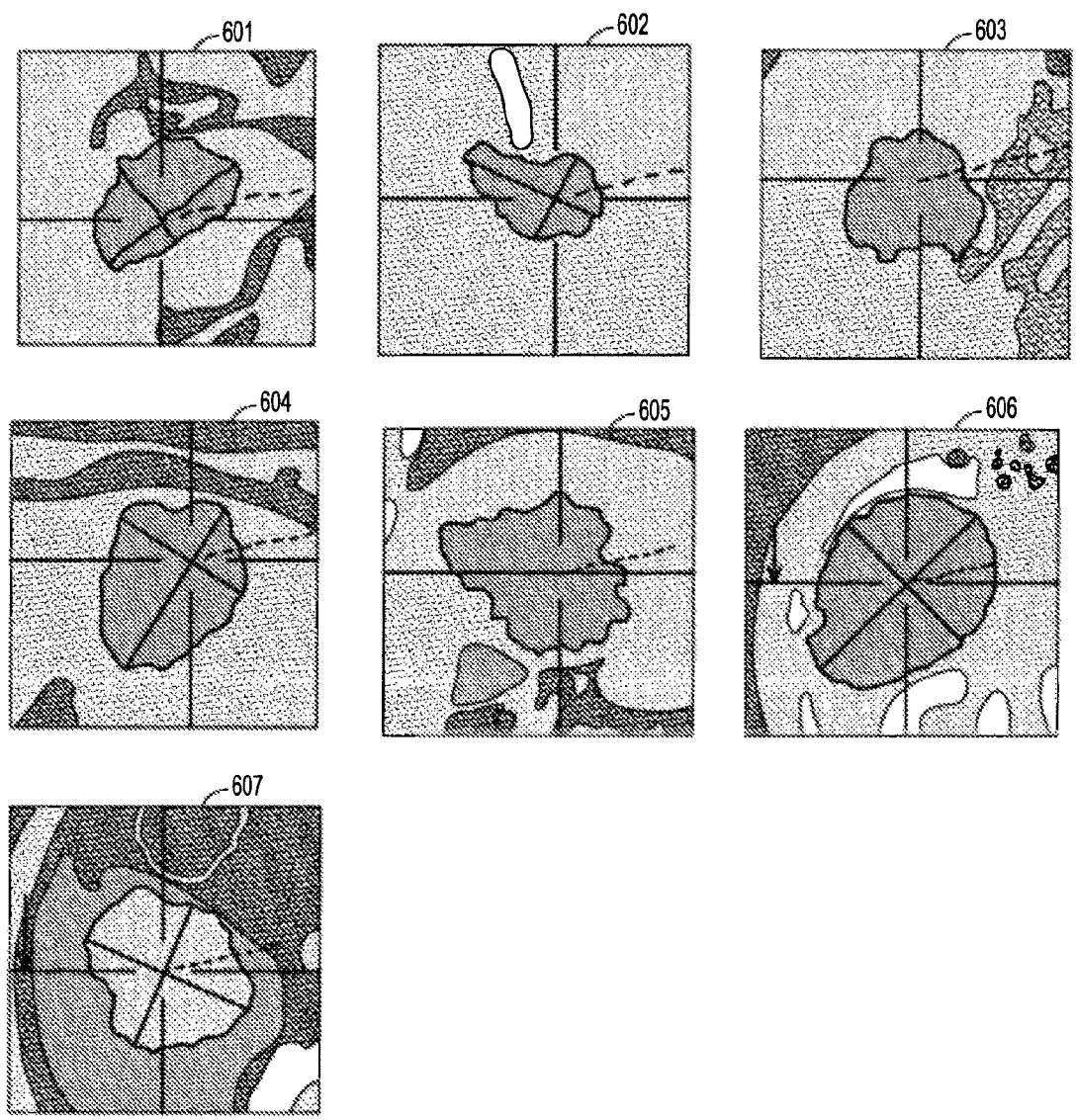
FIGS. 6-12 illustrate different segmentations of objects from a background in 3D image data in accordance with one or more aspects of the present invention.
Figure 7:
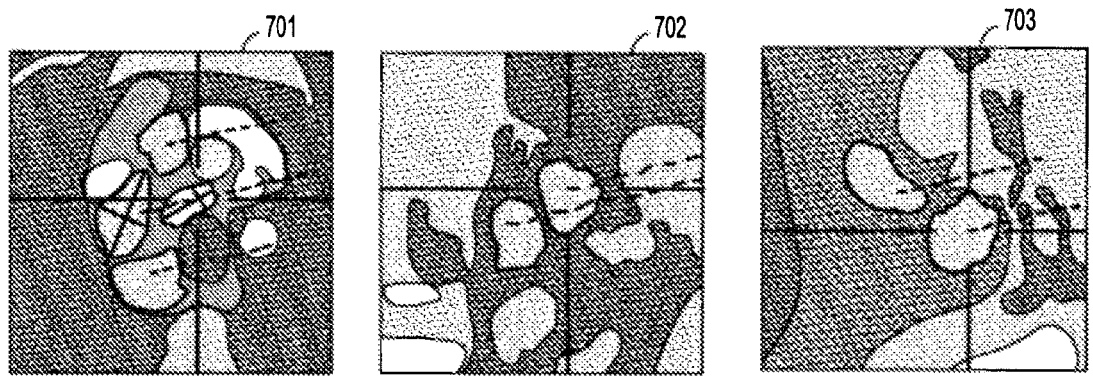
Figure 8:
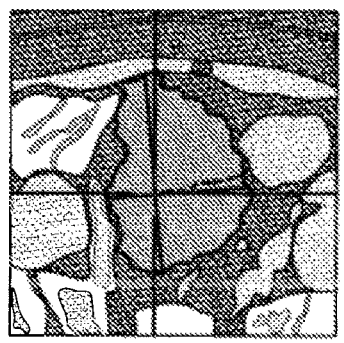
Figure 9:
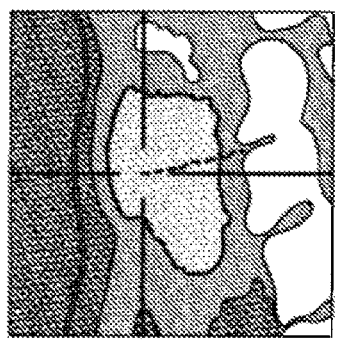
Figure 10:
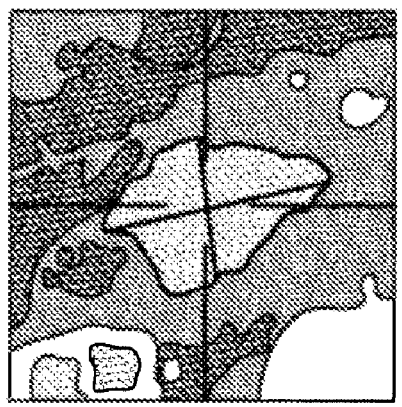
Figure 11:
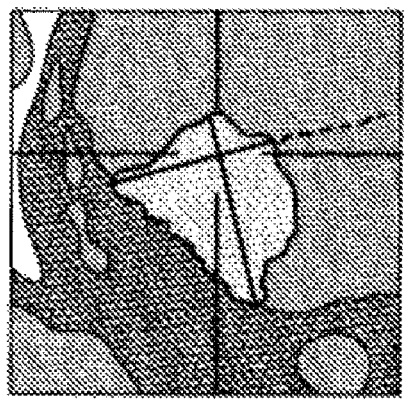
Figure 12:
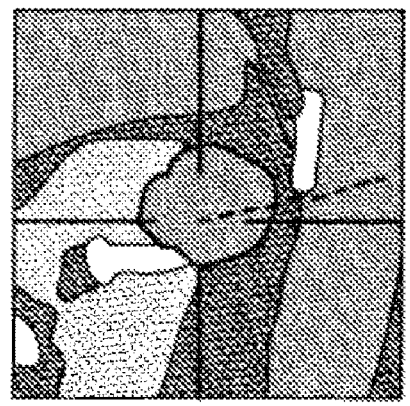

Segmentation results are shown in FIGS. 6-12. In FIG. 6, the 7 images 601, 602, 603, 604, 605, 606, and 607 are liver lesions. Image 607 shows a hyperdense lesion and image 605 shows a lesion with a necrotic core. The images in the figures show the contours achieved by applying segmentation in accordance with one or more aspects of the present invention. Some contours in the images such as in FIGS. 6, 9 and 12 are highlighted to improve contrast of the contour in black and white print. In FIG. 7 images 701, 702 and 703 show images of lymph nodes and segmentation contours achieved in accordance with one or more aspects of the present invention. FIG. 8 shows an image and a segmentation contour of an ovarian lesion. FIG. 9 shows an image and a segmentation contour of a thyroid lesion. FIG. 10 shows an image and a segmentation contour of a pancreas lesion. FIG. 11 shows an image and a segmentation contour of a bladder lesion. FIG. 12 shows an image and a segmentation contour of a kidney lesion.

Figure 13:
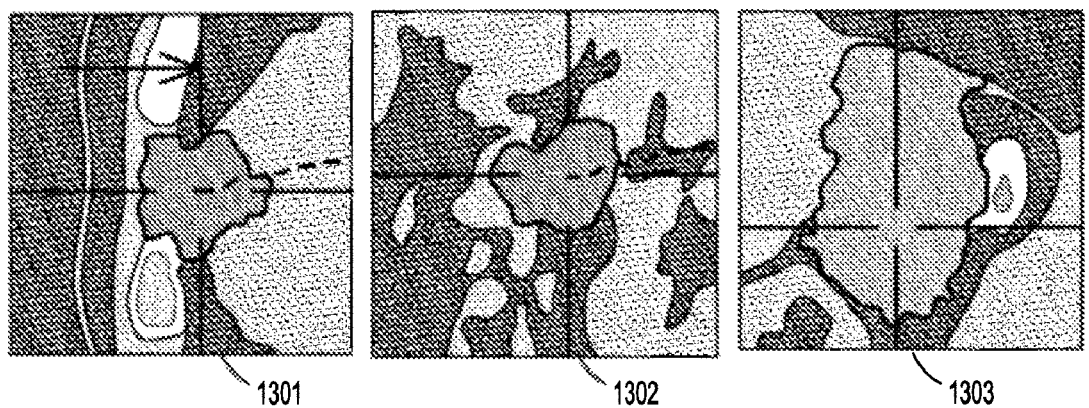
FIG. 13 illustrates an effect of a segmentation of an object from a background in 3D image data in accordance with an aspect of the present invention.

The segmentation method, which is an aspect of the present invention, produces very good results on all these lesions. FIG. 13 shows 3 examples in images 1301, 1302 and 1303 where the segmentation results are not as good. In all three cases, the algorithm has leaked into neighboring structures that are very similar in gray level. The segmentation contour in image 1303 has been highlighted.

To evaluate the performance of the algorithm quantitatively, the following measures between the ground truth and the automatic segmentation were computed. The normalized volume difference is defined as $$V_d = \frac{|V_A - V_{GT}|}{V_{GT}},$$

wherein $V_A$ is the automatically segmented volume, and $V_{GT}$ is the ground truth volume. The volume overlap reflects the relative position of the two objects better and is defined as $$V_o = \frac{V_A \cap V_{GT}}{V_A \cup V_{GT}}.$$

Figure 14:
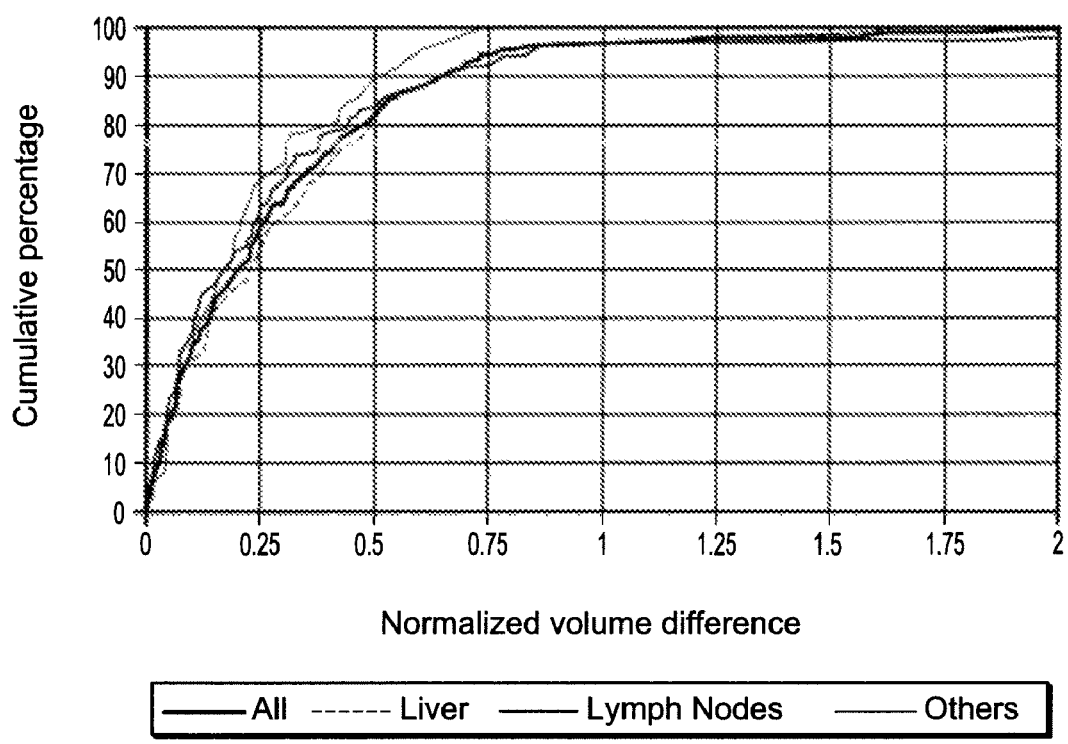
FIGS. 14-16 illustrate the performance of segmentation in accordance with at least one aspect of the present invention.

FIG. 14 shows the cumulative histogram of normalized volume differences between segmented and ground truth lesions over all lesions (bold curve). This curve basically shows that in 50% of the cases, the normalized volume difference is below 25% (18.5% to be exact) and in 80% of the cases, it is below 50%. The figure also displays the cumulative histograms of the same quantity for liver lesions, lymph nodes, and other lesions. It can be seen that the type of lesion does not influence the behavior of the algorithm. Other lesions are segmented better probably because 20 of them are lung lesions which have high contrast and are relatively easier to segment.

Figure 15:
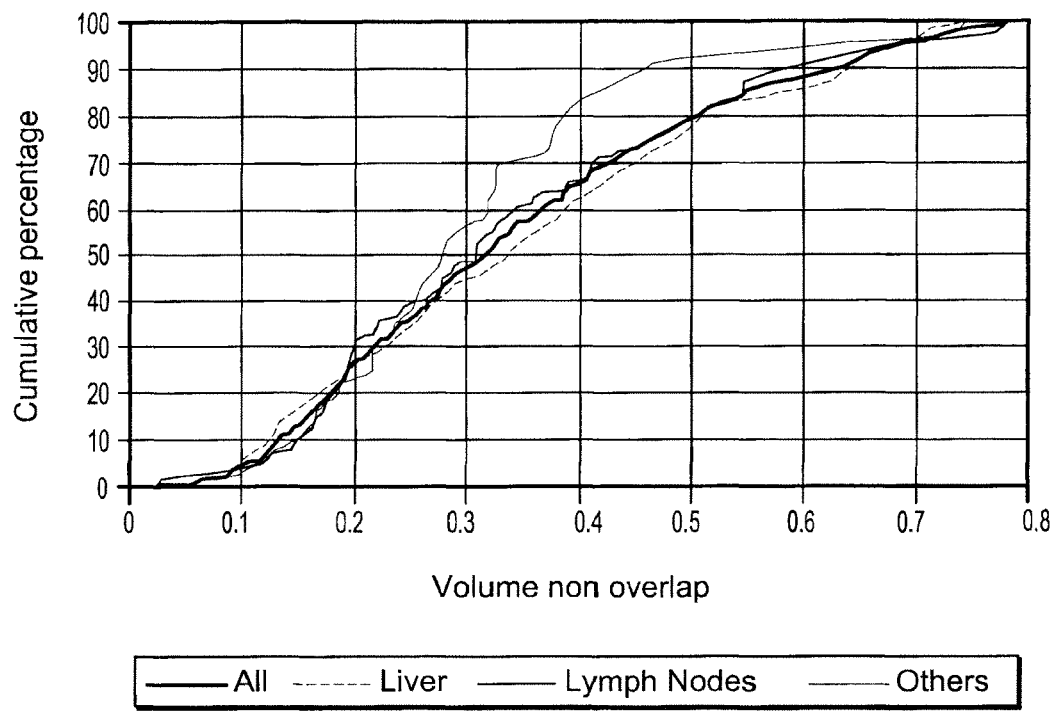

FIG. 15 shows the cumulative histogram of volume non overlap (1-$V_O$) between segmented and ground truth lesions over all lesions (bold curve), liver lesions, lymph nodes, and other lesions. Again, it can be seen that the algorithm perform roughly the same on all lesions, slightly better on other lesions. From visual inspection of segmented objects, radiologists agree that a volume non overlap of 30% is good, 30 to 60% is acceptable, and 60% or higher is poor. It can be seen that 90% of the segmented lesions fall in the good to acceptable zone and 50% of the lesions are well segmented.

Figure 16:
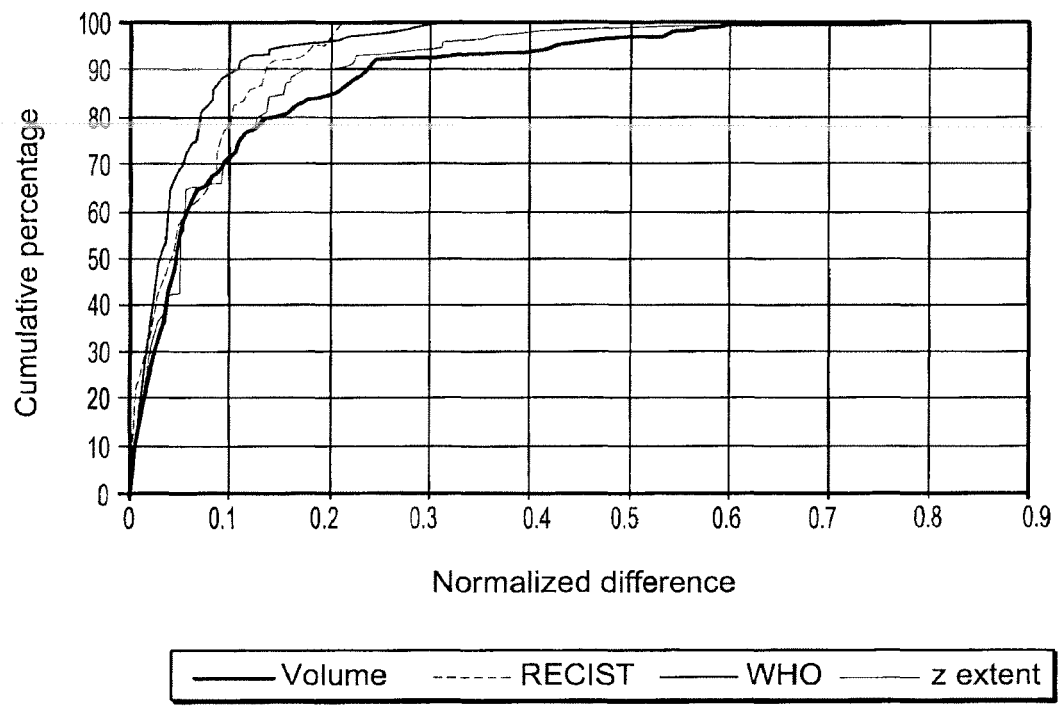

From the binary 3D segmentation, the system automatically computes the volume, RECIST and WHO diameters and Z-extent of the lesion. To evaluate the accuracy of the measurements, a physical phantom containing 31 lesions (spherical and gelcap shaped) of different known sizes was scanned, with a slice thickness of 2 mm. Each of the lesions was segmented using 10 different initialization strokes. Next the normalized difference in volume, RECIST diameter, WHO diameter and Z-extent between the known measurements and the calculated measurements were computed. The cumulative histogram for all 10 runs on all 31 lesions is shown in FIG. 16. It can be seen that in 90% of the cases, the WHO diameter is within 10% of the true diameter, the RECIST diameter within 15% of the true RECIST diameter, and the volume within 25% of the true volume.

Figure 17:
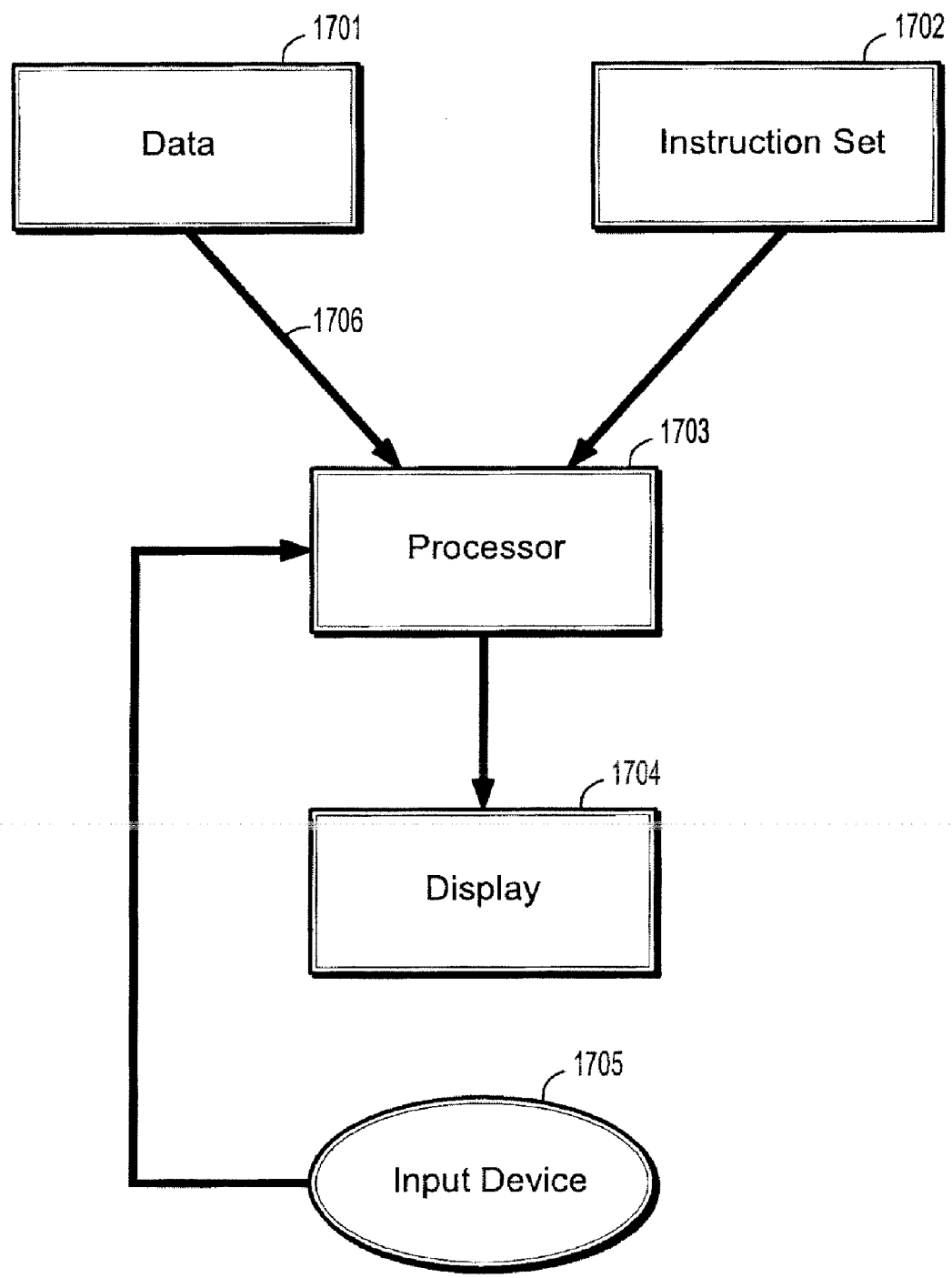
FIG. 17 illustrates a computer system for performing the steps described herein in accordance with another aspect of the present invention.

The image segmentation that is provided as an aspect of the present invention can be executed by a system as shown in FIG. 17. The system is provided with data 1701 representing image data. Such image data may be CT data. It may be stored in a memory so that 1701 is a memory with image data. Image data may be provided on an input 1706 to a processor 1703. An instruction set or program 1702 executing the methods of the present invention is provided. The instruction set may be stored in memory so that 1702 may be a memory with instruction data and made available from memory to processor 1703, which can process the instructions of 1702 and apply it to the data 1701, which may also be stored in a memory. An image, such as a segmented image can be output on a device 1704. Such a device for instance can be a display. The processor can be dedicated hardware. However, the processor can also be a CPU or any other computing device that can execute the instructions of 1702. An input device 1705 like a mouse, or track-ball or other input devices may be present to allow a user to for instance place foreground and background seeds in an image provided for instance on the display 1704 for processing by the processor. The input device may also be used to start or stop instructions on the processor. Accordingly, the system as shown in FIG. 17 provides a system for image segmentation using methods disclosed herein.

The term pixel herein also intends to cover the term voxel.

The following references are generally descriptive of the background of the present invention and are hereby incorporated herein by reference: [1] World Health Organization, "WHO handbook for reporting results of cancer treatment," 1979; [2] P. Therasse, S. G. Arbuck, E. A. Eisenhauer, J. Wanders, R. S. Kaplan, L. Rubinstein, J. Verweij, M. van Glabbeke, A. T. van Oosterom, M. C. Christian, and S. G. Gwyther, "New guidelines to evaluate the response to treatment in solid tumors," Journal of the National Cancer Institute, vol. 92, no. 3, pp. 205-216, 2000; [3] L. van Hoe, E. van Cutsem, I. Vergote, A. L. Baert, E. Bellon, P. Dupont, and G. Marchal, "Size quantification of liver metastases in patients undergoing cancer treatment: reproducibility of one-, two-, and three-dimensional measurements determined with spiral CT," Radiology, vol. 202, no. 3, pp. 671-675, 1997; [4] P. J. Yim and D. J. Foran, "Volumetry of hepatic metastases in computed tomography using the watershed and active contour algorithms," in Proc. IEEE Symposium on Computer-Based Medical Systems, New York, N.Y., 2003, pp. 329-335; [5] M. Bilello, S. B. Gokturk, T. Desser, S. Napel, R. B. Jeffrey Jr., and C. F. Beaulieu, "Automatic detection and classification of hypodense hepatic lesions on contrast-enhanced venous-phase CT," Medical Physics, vol. 31, no. 9, pp. 2584-2593, 2004; [6] J. Dornheim, H. Seim, B. Preim, I. Hertel, and G. Strauss, "Segmentation of neck lymph nodes in CT datasets with stable 3D mass-spring models," in Proc. MICCAI, 2006, pp. 904-911; [7] G. Unal, G. Slabaugh, A. Ess, A. Yezzi, T. Fang, J. Tyan, M. Requardt, R. Krieg, R. Seethamraju, M. Harisinghani, and R. Weissleder, "Semi-automatic lymph node segmentation in LN-MRI," in Proc. Int. Conf. Image Processing, Atlanta, Ga., 2006, pp. 77-80; [8] J. K. Udupa and S. Samarasekera, "Fuzzy connectedness and object definition: Theory, algorithms, and applications in image segmentation," Graphical Models and Image Processing, vol. 58, no. 3, pp. 246-261, 1996; [9] G. T. Herman and B. M. Carvalho, "Multiseeded segmentation using fuzzy connectedness," IEEE Trans. Pattern Analysis and Machine Intelligence, vol. 23, no. 5, pp. 460-474, 2001; [10] L. Grady, "Random walks for image segmentation," IEEE Trans. Pattern Analysis and Machine Intelligence, vol. 28, no. 11, pp. 1768-1783, 2006; [11] L. Grady and G. Funka-Lea, "An energy minimization approach to the data driven editing of presegmented images/volumes," in Proc. MICCAI, 2006, pp. 888-895; [12] Y. Li, S. Hara, and K. Shimura, "A machine learning approach for locating boundaries of liver tumors in {CT} images", Proc. Int. Conf. on Pattern Recognition, vol. 1, pp. 400-403, 2006.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims appended hereto.

The invention claimed is:

1. A method for segmentation of an object from a background in three-dimensional (3D) image data, comprising:

initiating at least one seed in the object in a two-dimensional (2D) representation of the 3D image, the at least one seed defines the object;

determining a distribution of intensity levels of pixels in the 2D representation of the 3D image relative to an intensity level of the at least one seed;

segmenting the object from the background in the 2D representation of the 3D image based on the distribution of intensity levels into a first 2D segmentation contour;

establishing a 2D segmentation contour of the object in at least two additional 2D representations of the image, such that each 2D representation contains the at least one seed in the object; and creating a 3D segmentation contour of the object by applying a random walker segmentation method to all pixels in the 3D image, using pixels inside the 2D segmentation contours as object seeds and pixels outside the 2D segmentation contours as background seeds;

determining a cost image $C_L$ associated with the at least one seed in the 2D representation of the object;

determining an object histogram $H_L$ associated with the cost image as the distribution of intensity levels of pixels:

computing a response image of the 2D representation of the object by applying an expression:

$$g(x, y) = \begin{cases} H_L(f(x, y))\left(1 - \frac{C_L(x, y)}{C_L^{max}}\right) & \text{if } L(x, y) = 1 \\ H_L(f(x, y))/2 & \text{if } L(x, y) = 0. \end{cases}$$

2. The method as claimed in claim 1, further comprising:
determining a background histogram $H_B$ for pixels not being part of the object in the 2D representation.

3. The method as claimed in claim 2, wherein the establishing of a 2D segmentation contour of the object in at least two additional 2D representations of the 3D image data using a response image that can be computed from an expression:

$$g(x, y) = \begin{cases} g(x, y) & \text{if } H_L(f(x, y)) > H_B(f(x, y)) \\ \text{else} \\ \frac{3H_L(f(x, y))}{4}\left(1 - \frac{C_L(x, y)}{C_L^{max}}\right) & \text{if } L(x, y) = 1 \\ H_L(f(x, y))/4 & \text{if } L(x, y) = 0. \end{cases}$$

4. The method as claimed in claim 1, wherein the 3D image data is provided by a CT scanner.

5. A method for segmentation of an object from a background in three-dimensional (3D) image data, comprising:

initiating at least one seed in the object in a two-dimensional (2D) representation of the 3D image, the at least one seed defines the object;

determining a distribution of intensity levels of pixels in the 2D representation of the 3D image relative to an intensity level of the at least one seed;

segmenting the object from the background in the 2D representation of the 3D image based on the distribution of intensity levels into a first 2D segmentation contour;

establishing a 2D segmentation contour of the object in at least two additional 2D representations of the image, each 2D representation containing the at least one seed in the object; and creating a 3D segmentation contour of the object by applying a random walker segmentation method to all pixels in the 3D image, using pixels inside the 2D segmentation contours as object seeds and pixels outside the 2D segmentation contours as background seeds;

determining a cost image $C_L$ associated with the at least one seed in the 2D representation of the object;

determining an object histogram $H_L$ associated with the cost image as the distribution of intensity levels of pixels;

determining a background histogram $H_B$ for pixels not being part of the object in the 2D representation wherein the establishing of a 2D segmentation contour of the object in at least two additional 2D representations of the 3D image data using a response image is computed from an expression:

$$g(x, y) = \begin{cases} g(x, y) & \text{if } H_L(f(x, y)) > H_B(f(x, y)) \\ \text{else} \\ \frac{3H_L(f(x, y))}{4}\left(1 - \frac{C_L(x, y)}{C_L^{max}}\right) & \text{if } L(x, y) = 1 \\ H_L(f(x, y))/4 & \text{if } L(x, y) = 0. \end{cases}$$

6. The method as claimed in claim 5, wherein the 3D image data is provided by a CT scanner.

* * * * *